United States Patent
Rousseau et al.

(10) Patent No.: US 12,370,008 B2
(45) Date of Patent: Jul. 29, 2025

(54) SYSTEM AND METHOD FOR PROVIDING A MEDICAL DEVICE

(71) Applicant: SUPERSONIC IMAGINE, Aix-en-Provence (FR)

(72) Inventors: Etienne Rousseau, Aix en Provence (FR); Matthieu Valentin, Marseilles (FR); Damien Majorel, Ales (FR); Damien Lerat, Aix-en-Provence (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 31 days.

(21) Appl. No.: 18/560,074

(22) PCT Filed: May 6, 2022

(86) PCT No.: PCT/EP2022/062336
§ 371 (c)(1),
(2) Date: Nov. 9, 2023

(87) PCT Pub. No.: WO2022/238264
PCT Pub. Date: Nov. 17, 2022

(65) Prior Publication Data
US 2024/0238061 A1 Jul. 18, 2024

(30) Foreign Application Priority Data
May 12, 2021 (EP) .................................. 21315084

(51) Int. Cl.
*A61B 50/24* (2016.01)
*A61B 8/00* (2006.01)
*A61B 8/08* (2006.01)

(52) U.S. Cl.
CPC .............. *A61B 50/24* (2016.02); *A61B 8/56* (2013.01)

(58) Field of Classification Search
CPC ......... A61B 50/24; A61B 8/56; A61B 8/4218; A61B 8/44; A61B 8/4477; A61B 8/4209
See application file for complete search history.

(56) References Cited

U.S. PATENT DOCUMENTS

2009/0247870 A1* 10/2009 Amemiya .............. A61B 8/467
600/437
2010/0152589 A1* 6/2010 Asai ....................... A61B 50/10
600/459

(Continued)

FOREIGN PATENT DOCUMENTS

JP 2004049588 A 2/2004
KR 20180034969 A * 4/2018
WO WO-2020239979 A1 * 12/2020 ........... A61B 8/0808

OTHER PUBLICATIONS

KR-20180034969 machine translation (Year: 2018).*

(Continued)

*Primary Examiner* — Alexei Bykhovski
(74) *Attorney, Agent, or Firm* — Merchant & Gould P.C.

(57) ABSTRACT

The invention relates to a system for providing a medical device, the system including a mounting structure arranged adjacent to and/or at least partially above an access space where an object to be accessed by the medical device can be placed, a holding device retained by the mounting structure and configured to hold the medical device at a changeable position above the access space, wherein the holding device is configured such that the medical device is moved from a retracted position to a first extended position upon a first predefined event.

23 Claims, 9 Drawing Sheets

(56) References Cited

U.S. PATENT DOCUMENTS

| | | | |
|---|---|---|---|
| 2011/0190635 A1* | 8/2011 | Bosler | A61B 8/4281 |
| | | | 600/458 |
| 2014/0001234 A1 | 1/2014 | Shelton et al. | |
| 2016/0121156 A1* | 5/2016 | Bach | A63B 21/0087 |
| | | | 482/112 |
| 2018/0279992 A1* | 10/2018 | Frankel | A61G 13/101 |
| 2019/0069842 A1 | 3/2019 | Rothberg et al. | |
| 2019/0307423 A1* | 10/2019 | Han | F16M 13/022 |
| 2020/0289230 A1* | 9/2020 | Denlinger | A61B 34/74 |

OTHER PUBLICATIONS

PCT International Preliminary Report on Patentability in Application PCT/EP2022/062336, mailed Nov. 23, 2023, 11 pages.
International Search Report and Written Opinion for PCT/EP2022/062336, Nov. 17, 2022, 16 pages.

* cited by examiner

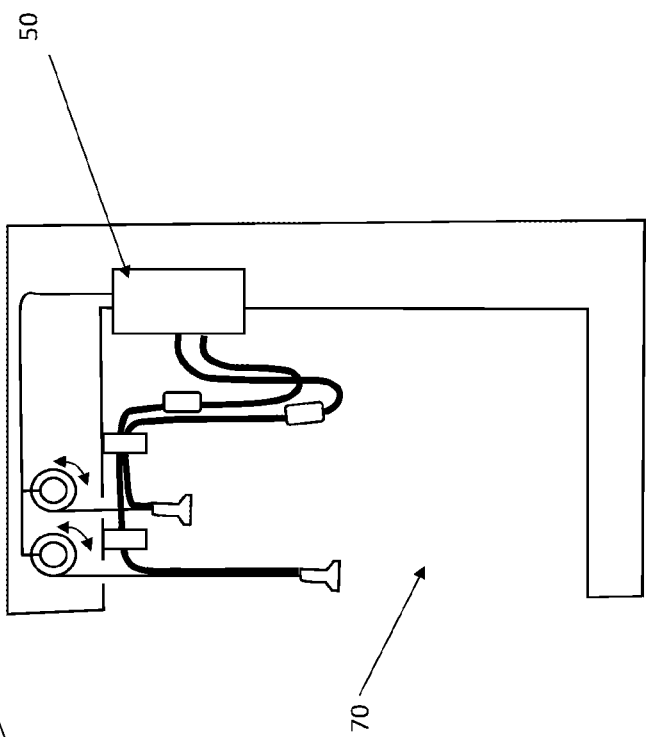
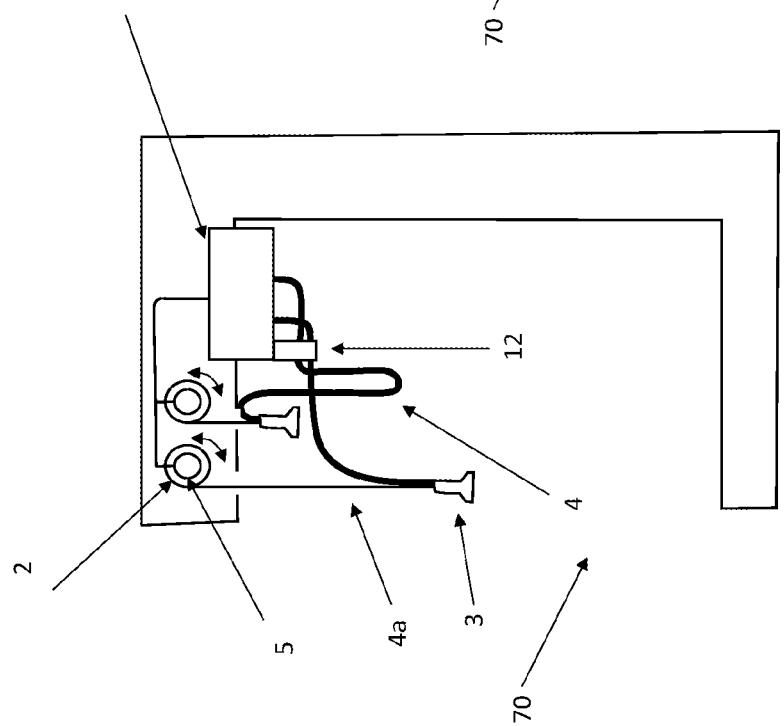
Fig. 5a
Fig. 5b

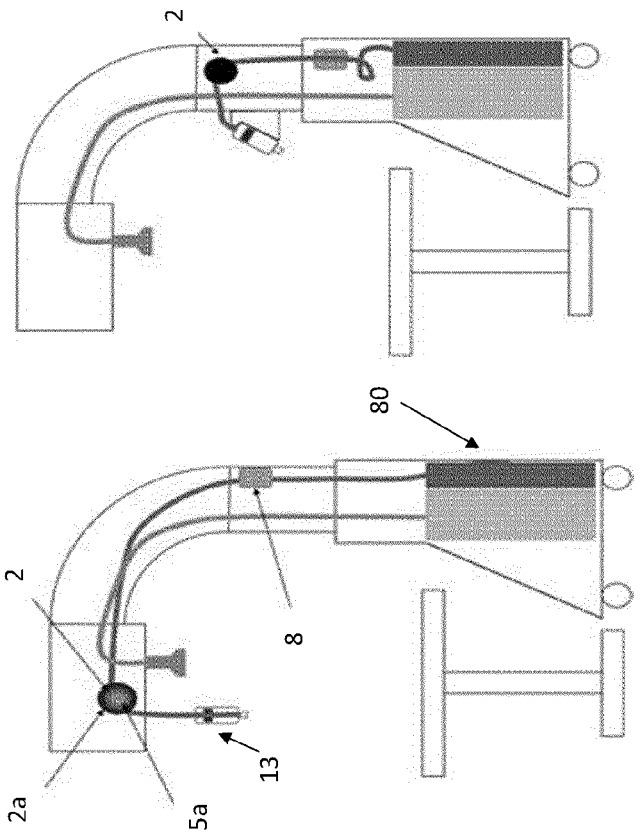
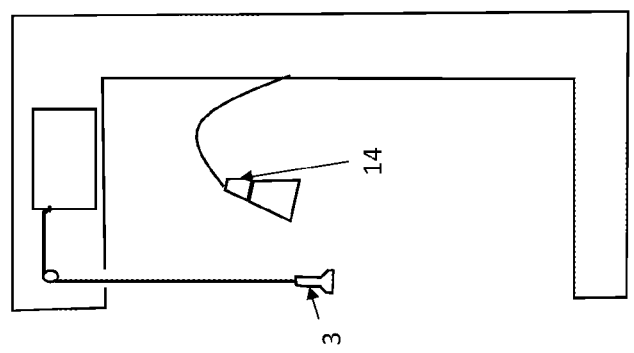

SYSTEM AND METHOD FOR PROVIDING A MEDICAL DEVICE

CROSS-REFERENCES TO RELATED APPLICATIONS

This application is a National Stage Application of PCT/EP2022/062336, filed on May 6, 2022, which claims the benefit of priority to EP Application Serial No. 21315084.0, filed May 12, 2021, each of the above applications being incorporated herein by reference in its entirety. To the extent appropriate, a claim of priority is made to each of the above disclosed applications.

FIELD OF THE DISCLOSURE

The present disclosure relates to a system and method for providing a medical device. In particular, the present disclosure concerns electric and/or electronic medical devices, such as for example an ultrasound examination probe, which comprise a cable for power supply and/or data communication. The medical device may allow a medical treatment and/or a medical examination.

BACKGROUND OF THE DISCLOSURE

Medical treatments or examinations are often assisted or achieved by medical devices. Such devices may be electric, for example for transforming electric power into heat or another energy during a medical treatment, and/or electronic, for example for collecting data during an examination and/or controlling the device. For this purpose, the medical device may comprise in some cases a cable for electric power supply and/or data communication. Accordingly, the cable connects the medical device to an external device, for example a power unit and/or a processing unit.

Exemplary users of medical devices are medical specialist such as doctors, veterinarian and radiologist specialized professionals, for example sonographers. The sonographers typically operate medical devices in the form of special imaging equipment to examine a human body by creating images or by conducting measurements and/or tests.

One example of dedicated imaging equipment is an ultrasound imaging system. Other examples include medical imaging system using mammography, tomography or MRI. In other words, medical examination is often assisted by computer implemented imaging methods. For this purpose, examination data from an examined body or medium (for example stones, animals, human body or part of it) is acquired and processed, in order to present it to the examining user or to another user such as a doctor or a surgeon.

For example, ultrasound imaging consists of an insonification of a medium with one or several ultrasound pulses (or waves) which are transmitted by an ultrasound probe comprising at least one ultrasound transducer. In response to the echoes of these pulses, ultrasound signal data are acquired, for example by using the same transducer.

Conventional ultrasound probes comprise a cable for both power supply (i.e. for generating pulses) and for data communication (i.e. transmitting echoes to an ultrasound processing unit). Such probes may be considered as passive and analogue, i.e. which may merely transmit acquired signals to a processing means but which may not themselves (totally or partially) compute data.

These conventional ultrasound probes are able to acquire data allowing high quality images generation, but they imply several restrictions. In particular, the required probe cable has a minimum thickness of for example 5 or 15 mm, in order to allow data communication via analog ultrasound signals. This leads to a particularly heavy cable. Another consequence is that the cable cannot be winded arbitrarily but has limited bending capabilities also due to an increased stiffness of the cable material. Another drawback is that the maximum length of the cables may be limited due to signal attenuation or other effects in the cable. Still another problem is that the signal transmission via such cables may be disturbed by electromagnetic emission in the environment. This may be in particular the case, when a cable is not hold and may therefore be close to another device which generates electromagnetic emission.

There further exist so-called "intelligent" probes which may be considered as active and digital. In particular, this type of probe comprises an own processing unit to process and optionally digitalize the acquired signals. The resulting data may then be transmitted via a wireless communication means (for example Bluetooth®, or WIFI) or a data cable (for example an electrical or optical wire) to an external processing and/or imaging unit. Such a probe may be autonomous in energy by comprising a battery (for example a rechargeable battery). However, due to the increased power consumption required by ultrasound technology, it may also comprise an external power supply in form of a power cable connected to an external power unit. Hence, power supply and data exchange may be realized by different (power and data) cables and/or connections.

A disadvantage of many medical devices is their weight, and in some cases also the weight of the cable. This is in particular important, when a user works frequently with the device, for example several hours per day. During examination of a patient, the user may have to access different parts of the patient's body, thereby holding the device in unnatural positions. In particular, the user is required to hold the medical device and at least a part of the cable during use what can lead to musculoskeletal problems due to the weight and unnatural holding positions. In some cases, the user puts the cable over one shoulder during use what however leads to an asymmetric physical load and can deteriorate the user's freedom of movement.

This is even more problematic, in case the cable is connected to a power unit and/or a processing unit which is positioned close to the ground floor and/or below the examination space, i.e. the region of interest, where the patient is situated. In this case a holder for an unused medical device may also be positioned in a lower region, such that the user has to lift the probe together with at least a part of the cable each time the probe is used. Lifting may be in particular tiring and/or annoying for the use due to the weight of the probe and/or its cable.

A further risk is that the medical device may accidentally be dropped by the user, for example due to the cable being below the patient or the user and close to the ground floor. The user may for instance accidentally step on the cable, such that the medical device falls down. The medical device may also, when moved from one place to another one, damage the cables, probes, . . . . As a consequence, the cable and/or the medical device may be damaged.

There exist different known techniques for providing ultrasound probes or accommodating probe cables. For example, US2010152589A1 describes a probe cable accommodation apparatus with a receptacle housing accommodating a plurality of probe cables. Each of the probe cables is connected at one end thereof to an ultrasound diagnostic system and has at an opposite end thereof an ultrasound probe. The interior of the receptacle housing is partitioned by a partition plate to form a plurality of receptacle chambers. The probe cables are accommodated in the receptacle chambers respectively.

JP2004049588A refers to a probe cable stowing device for an ultrasonograph which hardly exposes a probe cable when it is not necessary. For this purpose, when a probe is used for a diagnosis, an operator pulls the probe cable toward the outside of a stowing chamber. A weight pulley is pulled upward due to the movements of the probe cable and is fixed to an upper position by the magnetic force between an iron piece and a magnet.

SUMMARY OF THE DISCLOSURE

Currently, it remains desirable to overcome the aforementioned problems and in particular to provide a system and method for providing a medical device which physically relieves the user from (manually) pulling or lifting the probe and/or (if existing) its cable(s). More in particular, the medical device is desirably automatically provided or ejected to a region of interest when needed, i.e. to an access space where an object to be accessed by the medical device (for example a patient) can be placed.

Therefore, according to the embodiments of the present disclosure, a system for providing a medical device is provided. Said system comprises:
  a mounting structure arranged adjacent to and/or at least partially above an access space where an object to be accessed by the medical device can be placed,
  a holding device retained by the mounting structure and configured to hold the medical device at a changeable position above the access space, wherein the holding device is configured such that the medical device is moved from a retracted position to a first extended position upon a first predefined event.

By providing such a system, it becomes possible to provide a medical device at the desired region of interest (i.e. above or close the access space). This may be done automatically by the system when the medical device is needed, i.e. upon a first predefined event.

In other words, the holding device may be configured to actuate upon a first predefined event such that the probe is moved from the retracted position to the first extended position.

In still other words, the system may be configured to actuate the holding device to move the probe from the retracted position to the first extended position upon the first predefined event.

Since the holding device holds the medical device above the access space, gravity may be used to approach the medical device toward the object to be accessed (for example for examination, diagnosis and/or treatment with the medical device). In other words, the medical device may be considered as "falling from the sky in the hands of the user". Accordingly, the user is physically relieved from manually pulling or lifting the probe and/or its optional cable.

As a further consequence, since the medical device is always hold by the holding device, it cannot fall down or be accidentally dropped by the user. Hence, the risk of accidentally damaging the medical device can be drastically reduced.

The first extended position may be closer to the access space, and/or below the retracted position. Accordingly, the medical device may be advantageously moved due to gravity towards the first extended position and hence towards the access space.

The medical device may comprise at least one of: an electric and/or electronic medical device, an examination probe, a medical sensor, a laser device and an ultrasound examination probe. As described below, the Accordingly, the medical device may be an electronic probe configured for a medical examination and/or diagnosis or to be used in this context (comprising for example medical accessories like an illumination element, a gel ejector and/or an disinfect dispenser as described below). Exemplary probes may be configured for ultrasound or mammography, tomography, MRI (magnetic resonance imaging) or other optical and/or acoustic technologies. The medical device may also be configured for any medical treatment, in particular one which requires electrical power supply and/or an electronic control of the device. The medical device may be for example a laser device. In one example, the medical device may be configured for cosmetic use.

The holding device may comprise at least one of:
  a medical device cable holder configured to move out a cable of the medical device upon the first predefined event, such that the medical device is moved from the retracted to the extended position,
  a tie holder and a tie configured to hold the medical device in the retracted position, wherein, upon the predefined first event the tie may be moved out by the tie holder, such that the medical device moves to the extended position,
  an electromagnet configured to hold the medical device in the retracted position, wherein upon the first predefined event the electromagnet is turned off, such that the medical device moves to the extended position, and
  a robotic arm configured to hold the medical device at the retracted position, wherein upon the first predefined event the robotic arm moves the medical device moves to the extended position.

Accordingly, the medical device may comprise a cable, for example for power supply and/or data communication. Said cable may be connected to an external unit, as described below. At the same time, the cable may be used to hold the device in any of its moveable positions. For this purpose, the system may comprise a respective cable holder. For example, the cable holder may be configured to move out the cable, in order to move the device from the retracted position to an extended position.

The medical device and its cable are desirably always hold by the holding device above the ground floor, i.e. in any of its possible positions. Hence, a user cannot accidentally step on the cable or the device. Hence, the risk of accidentally damaging the medical device and/or its cable can be reduced.

Alternatively, for example in case the medical device does not comprise a cable (but even in this case), the medical device may also be attached to a tie which holds the device in any of its moveable positions.

The mounting structure may comprise a first accommodation space configured to: accommodate the medical device cable holder and the cable of the medical device, such that the cable can be moved out by the medical device cable holder, and/or hide the cable within the mounting structure in the retracted position of the medical device. Accordingly, the medical device and the cable may be self-protected or protected from exterior influences.

The medical device cable holder may comprise at least one wheel and/or pulley, which moveably supports the medical device cable.

The cable holder may also comprise a plurality of wheels/pulleys to arrange the cable, for example in a folded manner or in a multiply folded manner (i.e. in a zig-zag form). In other words, the cable may be fold around the wheels/pulleys. The wheels/pulleys may be rotatable and/or transversely moveable, such that the distance between the wheels/pulleys is changeable.

The wheel(s)/pulley(s) may be arranged in different locations and/or orientations, in particular horizontally and/or vertically in the first accommodation space.

The wheel and/or pulley may have a minimum diameter which is defined as a function of a predetermined bendability parameter of the cable, the bendability parameter comprising among others at least one of: a cable thickness, a cable type, and a cable material (in particular the material of a wire comprised by the cable).

For example, the wheel/pulley may have a diameter of at least 6 cm, to respect the maximum bendability of the cable, in particular of a conventional ultrasound probe cable.

The system may further comprise an actuator configured to actuate the holding device, such that the medical device is moved from the retracted position to the first extended position upon the first predefined event.

Such an actuator may allow an automatic movement or may allow triggering an automatic movement (due to gravity) of the medical device. Accordingly, the user is advantageously not required to manually lift or pull the device.

The actuator may comprise at least one of:
- a hydraulic actuator, for example in the form of an extendable cylinder,
- an electronically and/or electrically controlled actuator,
- an electric motor,
- a linear motor, and
- any other type of electro-magnetic actuator like for example an electromagnet or electromagnetic pad (for example allowing triggering an automatic movement due to gravity).

The medical device may be connected via a data cable to a processing unit which processes medical data received from the medical device via the data cable, and the mounting structure comprises a second accommodation space configured to accommodate the processing unit above the access space.

This scenario is in particular interesting, in case a conventional ultrasound probe is used. In this case, the probe cable may namely be limited to a maximum length. However, by accommodating the processing unit inside the system, said maximum length may still be enough to allow a user to move the probe to any position in the access space.

The medical device may be connected via a power cable to a power unit which powers the medical device via the power cable, the power unit being accommodated in the mounting structure.

The power unit may be separate from processing unit, for example in case an intelligent probe (i.e. which processes or pre-processes and compresses signal data) is used, as described above. The processing unit may be remote and/or external to the system, for example in another box, room or building, and/or may be a central processing unit for several devices. However, the power unit may be close to the medical device or the system for permitting the required power supply.

The connectors of the processing unit and/or the power unit for connecting the cables may advantageously be accessible for a user (e.g. on an open backside of the system or via a portal). This allows easily connecting/disconnecting the probes, for example when a probe has to be replaced or added.

The system may further comprise a control unit configured to receive a command from a user or an external processing unit and to control in response the holding device and/or the actuator, such that the medical device is moved from the retracted position to the first extended position. The control unit may also be part of the processing unit or the power unit.

The medical device may wirelessly transmit medical data to a processing unit which is separate to the power unit and/or remote to the system.

In this scenario the medical device may be an intelligent probe, as described above. In other words, the medical device may be a probe configured to process the acquired signals and transmit processed data via a data cable or via an integrated wireless communication means to the processing unit. There is hence no restriction regarding a maximum allowed distance between the probe and the processing unit.

The mounting structure may comprise a third accommodation space configured to accommodate the medical device in its retracted position and/or above the access space. Accordingly, the third accommodation space may be arranged centrally above the access space, such that the medical device can reach the whole access space.

The third accommodation space may comprise a maintenance device configured for at least one of the following functions:
- disinfecting and/or cleaning the medical device (using for example ultraviolet waves and/or a disinfecting and/or cleaning liquid),
- testing and status control using at least one scanner to scan the medical device (for example at least one camera), and
- protecting the medical device from exterior influences (optionally comprising protection during transporting the system, at least from one room to another or from production site to hospital).

The distance between the second accommodation space via the first and third accommodation space to the access space may be less than a distance threshold which is defined as a function of a maximum length of the medical device cable (if any).

Accordingly, the configuration of the system allows the use of a medical device with a limited maximum length. Said maximum length and hence said distance may be for example around 2 m. Such a limited maximum length may be advantageous for several reasons: Since cables are rather expensive, the price of the medical system can be reduced. moreover, the longer the cable is, the more voltage drop there is, which forces to oversize a power supply (which is often complicated because the pulsers that generate the signals must also resist to these possibly higher voltages). There may thus be an increased signal attenuation in the cable. Furthermore, with an increased cable length, there is a risk of resonance phenomena which may break the probes or electronic parts of the processing unit. Hence, the cable length is limited by electronic restrictions. However, due to a required freedom of movement of the user, a minimum cable length is required. As a result, it has been found that an optimum length is around 2 m, or at least in the range of, 1.5 m to 3 m.

The system may be configured for providing a plurality of medical devices and may comprise a respective plurality of holding devices.

Each holding device may be retained by the mounting structure and configured to hold a medical device at a changeable position above the access space.

The system may be configured to actuate a first holding device among the plurality of medical devices to move a respective first medical device from the retracted position to the first extended position upon the first predefined event.

Accordingly, the first predefined event may not only trigger the movement of a medical device. It may also trigger the selection of a specific device among several medical devices. Hence, the level of automatization may be increased, as the user may not only automatically receive a medical device in a comfortable position but may also be relieved from selecting a suitable medical device. In other words, the system may be configured for automatically distributing medical devices. Accordingly, the system may provide in any situation of a medical examination or treatment a suitable medical device based on the present context. For example, the context may constitute a current medical workflow. As also described in the following, the system may be configured to select a specific medical device based on an algorithm comprising among others: a predefined and/or customisable medical workflow algorithm, and an artificial intelligence algorithm.

The holding device may be configured to move the medical device from the first extended position to a second extended position upon a second predefined event. The second extended position may be closer to the access space, and/or below the first extended position.

Accordingly, the holding device may be configured such that the medical device can be moved to at least three different positions:
- a retained position for maintenance and/or protection of the medical device, where the medical device is not or hardly reachable by a user,
- a first extended position which may be understood as a standby position above the access space (above the place where patient is or is supposed to be, with a predefined security distance), where a user can easily reach the medical device (with his hand(s)),
- a second extended position, where the medical device is more extended than in the first extended position for a minimum length defined as a function dimensions of the examination space (plus an optional amount for accessing the examined object from other directions than from above).

There may also be several second extended positions, in order to allow the user to increasingly (e.g. incrementally/stepwise) extend the medical device depending on the required examination access range.

The holding device may be configured to move the medical device from the first or second extended position to the retracted position upon a third predefined event.

This may be the case, when for example a procedure implying the use of the medical device has been ended or when the protocol used implies using several medical devices in a timely manner. Accordingly, the medical device may automatically be put away and/or stored in safe retracted position when not used.

The mounting structure may comprise: a fourth accommodation space configured for accommodating a gel reservoir connected via a gel tube to a gel ejector (for example a gel pistol), and a gel ejector holding device retained by the mounting structure and configured to hold the gel ejector at a changeable position above the access space.

The gel ejector holding device may be configured to move the gel ejector in at least one of the following ways:

from a retracted position to the first extended position upon a fourth predefined event,
from the first extended position to a second extended position upon a second predefined event, the second extended position being closer to the access space, and/or below the first extended position, and
from the first or second extended position to the retracted position upon a fifth predefined event.

Accordingly, the gel injector may be attached and be provided by the system in a similar way like the one or several medical devices.

The numbering of the accommodation spaces does not limit them to any order or positioning. In other words, the second, third and fourth accommodation space do not require any of the spaces with preceding numbers.

At least one of the first to fifth predefined events comprises at least one of: a user command (for example received by means of a voice recognition system, a touch screen, a button, a tablet, smartphone, etc.), a sensor signal, a command triggered by a predefined protocol/workflow, an algorithm comprising among others: a predefined and/or customisable medical workflow algorithm, and an artificial intelligence algorithm.

the second predefined event may comprise at least one of: a sensor signal from a sensor of the medical device or the ejector indicating that a user has touched the medical device or the ejector, and a sensor signal from a sensor indicating that a user has pulled the medical device or the ejector toward the second extended position.

For example, the medical device may be moved out to given position above patient, i.e. the first extended position, upon the first predefined event. Then the user may touch the medical device thereby triggering a touch sensor of the device what leads to moving the device to a second extended position. It is also possible that the user pulls the device with at least a predefined minimum force once, thereby triggering a tension sensor of the device what leads to moving the device to a second extended position, as well.

The third predefined event may comprise at least one of: the end of a predefined and/or customisable medical workflow, a user command stopping a current medical workflow or indicating that a current workflow is to be continued with another medical device, and a command triggered by an algorithm indicating that a current workflow is to be continued with another medical device.

User commands may also be triggered by a user via a pedal, touch screen, or remote control. Alternatively, an AI algorithm may be used to recognize any intended user commands. This AI algorithm may be previously trained based on known medical workflows and/or acquisition data and/or video data as example.

In case the third predefined event comprises a command that a current workflow is to be continued with another medical device, the first medical device may be retracted from the second extended position to the retracted position, and a second selected medical device is extended from the retracted position to the first extended position upon the third event.

The retraction of the first medical device and the extension of the second medical device may be done simultaneously.

The present disclosure further relates to a medical platform comprising a medical device, and a system according to any one of the preceding claims.

The medical platform may further comprise a processing unit configured to process medical data received from the medical device. The processing unit may for example be connectable to and/or configured to be associated with the medical device, for instance via a cable.

The processing unit may be configured to carry out a (for example predefined and/or customisable) medical workflow algorithm and/or an artificial intelligence algorithm, and to transmit a command to the system triggered by any of the algorithms.

The command may constitute at least one of the first, second, third and fourth predefined event.

The medical platform may further comprise any of the other above-mentioned elements, for example a cable of the medical device.

The medical platform may further comprise a user interface, like a keyboard and/or a touchscreen. It may further comprise at least one display (optionally with touch functionality such as touchpad). These devices may be linked, attached or be attachable to the mounting structure and/or retractable into it.

The medical platform may hence comprise the system according to the present disclosure together with a medical system, as described in context of the figures.

The present disclosure further relates to a method for providing a medical device comprising the following steps:
arranging a mounting structure adjacent to and/or at least partially above an access space where an object to be accessed by the medical device can be placed,
providing a holding device retained by the mounting structure, wherein
the holding device holds the medical device at a changeable position above the access space, and
the holding device actuates upon a first predefined event such that the medical device moves from a retracted position to a first extended position.

The method may comprise further method steps comprising to the system features described above.

The present disclosure further relates to a computer program comprising computer-readable instructions which, when executed by a data processing system, cause the data processing system to carry out the method according to the present disclosure.

The present disclosure may also relate to a recording medium readable by a computer and having recorded thereon a computer program including instructions for executing the steps of the method according to the present disclosure, when said program is executed by a computer.

The disclosure and its embodiments may be used in the context of medical devices dedicated to human beings, plants or animals but also any (non-living) material to be considered such as metallic pieces, gravel, pebbles, etc.

It is intended that combinations of the above-described elements and those within the specification may be made, except where otherwise contradictory.

It is to be understood that both the foregoing general description and the following detailed description are exemplary and explanatory only, are provided for illustration purposes and are not restrictive of the disclosure, as claimed.

The accompanying drawings, which are incorporated in and constitute a part of this specification, are provided for illustration purposes, and illustrate embodiments of the disclosure and together with the description and serve to support and illustrate the principles thereof.

BRIEF DESCRIPTION OF THE DRAWINGS

FIGS. 5a and 5b show a fifth exemplary embodiment of the system in two different configurations according to embodiments of the present disclosure;

FIGS. 9a and 9b show a ninth exemplary embodiment of the system in two different configurations according to embodiments of the present disclosure;

FIGS. 10a and 10b show an tenth exemplary embodiment of the system in two different configurations according to embodiments of the present disclosure.

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts. Moreover, the features explained in context of a specific embodiment, for example that one of FIG. 1, also apply to any one of the other embodiments, when appropriate, unless differently described.

Figure 1:
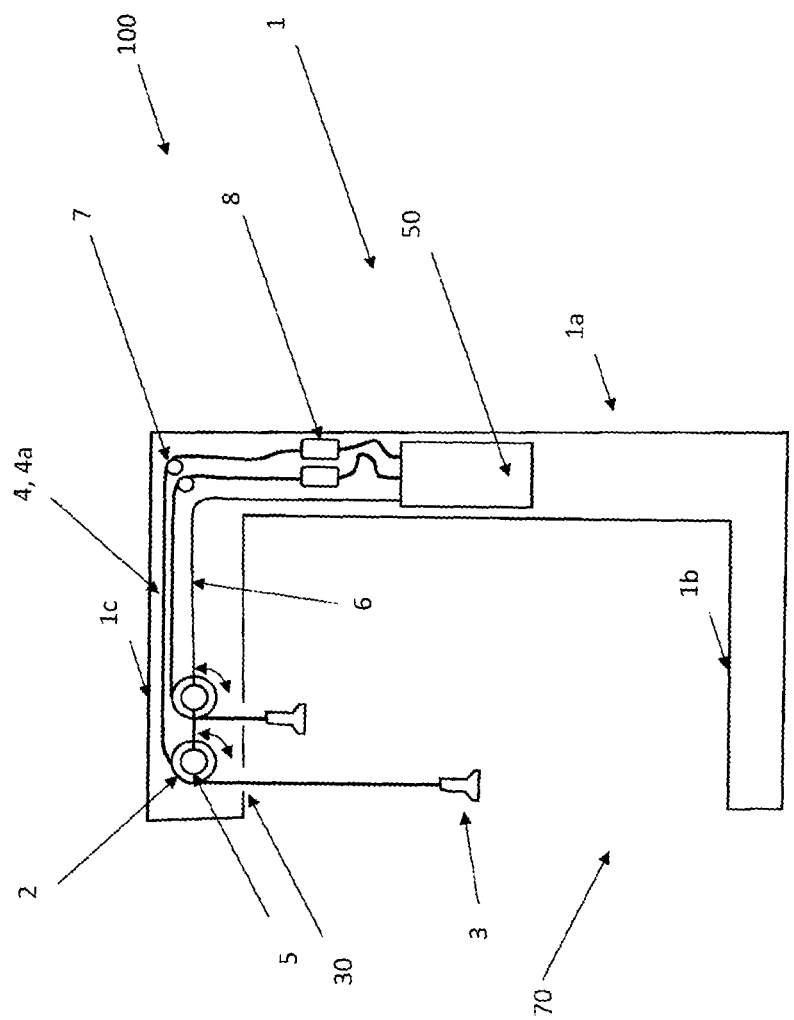
FIG. 1 shows a first exemplary embodiment of the system according to embodiments of the present disclosure.

FIG. 1 shows a first exemplary embodiment of the system according to embodiments of the present disclosure. The system 100 is configured for providing a medical device 3. Said system comprises a mounting structure 1 arranged adjacent to and/or at least partially above an access space 70 where an object to be accessed by the medical device can be placed. The system further comprises a holding device 2 retained by the mounting structure 1 and configured to hold the medical device 3 at a changeable position above the access space. The holding device 2 is configured such that the medical device 3 is moved from a retracted position to a first extended position upon a first predefined event.

In the present example, the system is configured to provide two medical devices 3, wherein one is schematically shown to be in an extended position and the other one in a retracted position. However, the system may also provide only one medical device or more than two, for example 2, 4 or 6. In the following description the system is explained with reference to one single medical device. Accordingly, the described features may exist in plurality depending on the number of existing medical devices.

The holding structure 1 may in particular extend in the vertical direction (for example from the ground floor), such that the holding device 2 can hold the medical device at a changeable position above the access space. In other words, the structure 1 may comprise a vertical extension part 1a. In one example, the holding structure 1 has substantially an L-form, where the L is upside down. In other words, the holding structure may have a horizontal branch, i.e. a horizontal extension part 1c on its top. In another example, as shown in FIG. 1., the structure 1 may have substantially a C-form. In other words, the structure may additionally have an enlarged base 1b. In this example, the structure additionally extends in a horizontal direction on its bottom side, in order to stabilize the structure. The structure 1, in particular its base may be configured to stand on the ground floor. The base may also serve for providing a seat or a stretcher to seat or place the object to be accessible by the medical device (for example a patient). The height of the structure may be for example 200 cm.

The holding structure may in particular be hollow and have in its inside one or several accommodation spaces, which are configured to accommodate at least some elements of a medical system. Said medical system may comprise for example the medical device 3, an optional cable 4 of the medical device, and an optional processing and/or power unit 50. Advantageously the holding structure has an opening 30 above the access space 70 configured to let the cable 4 and/or the medical device 2 pass from inside to outside. The opening may have a closeable door, as explained in context of FIG. 11a-d.

The processing and or power unit 50 may be arranged at different positions inside the structure (i.e. in arranged in a second accommodation space of the mounting structure according to the present disclosure), adjacent to it or remotely/externally. In the present example of FIG. 1, it is arranged in the vertical extension part 1a which may form a hollow column (for example in cylinder form or with a rectangular cross section). The cable 4 is thus extending inside the structure from the unit 50 toward the opening 30.

The medical device 3 may be an electronic probe configured for a medical examination and/or diagnosis, for example an ultrasound transducer. In other examples, it may be an electric and/or electronic medical device, an examination probe, and an ultrasound examination probe. In a further example, it may be an optical device, for example emitting a laser beam.

In this example, the medical device comprises a cable 4, for example for power supply and/or data communication. Said cable may be connected to another unit accommodated in the system, here a processing unit 50. At the same time, the cable may be used to hold the device in any of its moveable positions.

For this purpose, the system comprises a holding device 2 in the form of a cable holder (arranged in a first accommodation space of the mounting structure 1 according to the present disclosure, for example in its horizontal and/or vertical extension parts). For example, the cable holder may be configured to move out the cable, in order to move the device from the retracted position to an extended position. The cable holder 2 may comprise at least one wheel, roller, drum and/or pulley, which moveably supports the medical device cable. In other words, the cable can be rolled out by rotating the wheel 2.

The system is desirably configured such that the medical device and its cable are always hold by the holding device above the ground floor, i.e. even in any extended position. Hence, a user cannot accidentally step on the cable or the device. Hence, the risk of accidentally damaging the medical device or its cable can be reduced.

Alternatively, for example in case the medical device does not comprise a cable (but even in this case), the medical device may also be attached to a tie 4a which holds the device in any of its moveable positions. Accordingly, the medical system may be a conventional probe or an intelligent probe, as described above.

The system may further comprise an actuator 5 configured to actuate the holding device 2, such that the medical device is moveable. Such an actuator may generally allow an automatic movement or may allow triggering an automatic movement (due to gravity) of the medical device. Accordingly, the user is not required to manually lift or pull the device, i.e. physically force the medical device to move.

In the present example, the actuator is an electric motor which can rotate the wheel 2. In an alternative the actuator may comprise a shape memory alloy. In particular, the motor may be integrated into the wheel. The electric motor may further comprise a clutch to de-couple the motor from the wheel, to allow free rotation of the wheel. The actuator may have a power supply in form of a cable 6. Said cable may be branched to the unit 50 or to any other power supply unit. The actuator may also be autonomous by having a battery and being controllable wirelessly. It is also possible that the system comprises a battery configured for an operation of the system and/or the medical system, i.e. independent from any external power supply. Such a battery may then also serve as a power supply for the actuator.

Moreover, in the present example the cable 4 may be guided from the opening of the structure 1 via the wheel 2 towards the processing and/or power unit 50. At least one further rotatable wheel or pulley 7 may be used to guide the cable 4 in a moveable manner. In the vertical extension part 1a of the structure a weight 8 may be attached to the cable, in order to pull it down, when the medical device 3 is moved from its extended position to its retracted position. For example, the clutch of the motor 5 may be decoupled (upon a third predefined event according to the present disclosure), to allow the cable to be retracted due to the gravity impact on the weight 8. The structure may hence allow to accommodate the cable 4 in a wound/twisted form, when the medical device 3 is in its retracted position (as schematically shown in FIG. 1). It is also possible that the system comprises a device for winding the cable 4 in a guided manner, as it will be described in the following. Said device may be arranged in the vertical extension part of the structure and/or in its horizontal extension part.

The holding device 2 may be configured to move the medical device from the first extended position to a second extended position upon a second predefined event. The second extended position may be closer to the access space, and/or below the first extended position. Accordingly, the holding device may be configured such that the medical device can be moved to at least three different positions:
  a retained position for maintenance and protecting the medical device, where the medical device is not or hardly reachable by a user,
  a first extended position which may be understood as a standby position above the access space (above the patient with a predefined security distance), where a user can easily reach the medical device (with his hand(s)),
  a second extended position, where the medical device is more extended than in the first extended position for a minimum length defined as a function dimensions of the examination space 70 (plus an optional amount for accessing the examined object from other directions than from above).

In the following an exemplary medical system is described. The system may be configured for diagnosis and/or for treatment of a patient. It may in particular comprise special imaging equipment, for example an ultrasound imaging system. Other examples include medical imaging system using mammography or other optical and/or acoustic technologies. In another example, for patient treatment the system may be for treatment use and/or cosmetic use and comprise for example a medical device in the form of a laser device.

The medical system may comprise a processing and/or power unit 50, an acquisition system (for example a probe in the form of a transducer 3) and/or a visualisation system (for example one or several displays attached to the structure 1).

In one exemplary embodiment the processing unit and/or the visualisation system is external to the system 100, for example when a smartphone and/or tablet forms the processing unit and/or visualization system. In case the probe is an intelligent probe, it may be connectable to the processing system via the internet, the 'cloud', 4G or 5G protocols, WIFI, any local network or any other data contact or remote connection.

It is further possible that the processing system and the visualization system are remotely connectable, for example via the internet, the 'cloud', 4G or 5G protocols, WIFI, any local network or any other data contact or remote connection.

The processing unit may comprise for example a central processing unit (CPU) and/or a graphical processing unit (GPU) communicating with optional buffer memories, optionally a memory (MEM) linked to the central processing system; and optionally a digital signal processor (DSP).

The probe may comprise at least one ultrasound transducer, for example a single transducer configured to transmit a pulse and receive the medium (i.e. tissue) response. Also, it is possible to use a plurality of transducers and/or a transducer array. The array may be is adapted to perform a bidimensional (2D) imaging of the medium, but the array could also be a bidimensional array adapted to perform a 3D imaging of the medium. The transducer array may also be a convex array including a plurality of transducers aligned along a curved line. The same transducer(s) may be used to transmit a pulse and receive the response, or different transducers may be used for transmission and reception.

The processing and/or power unit 50 or an external processing unit may further be configured to control the movement of the medical device by respectively triggering the holding device 2 and/or the actuator 5. It may in particularly be configured to receive external commands, for example from a user interface (for example as described above). Such a command may constitute any of the above-described events. The processing and/or power unit 50 may also trigger any of the events by itself, for example based on a medical workflow algorithm or an AI algorithm which is carried out on the processing unit.

Figure 2B:
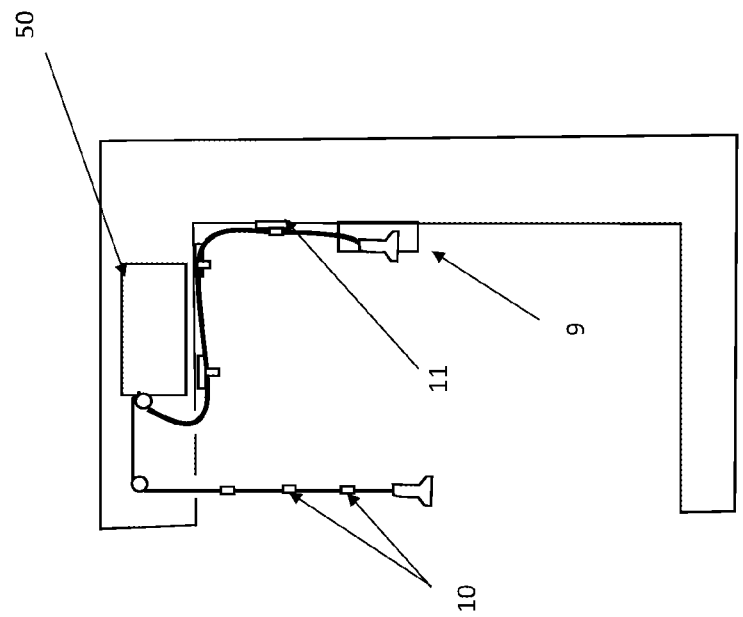
FIGS. 2a and 2b show a second exemplary embodiment of the system in two different configurations according to embodiments of the present disclosure.
Figure 2A:
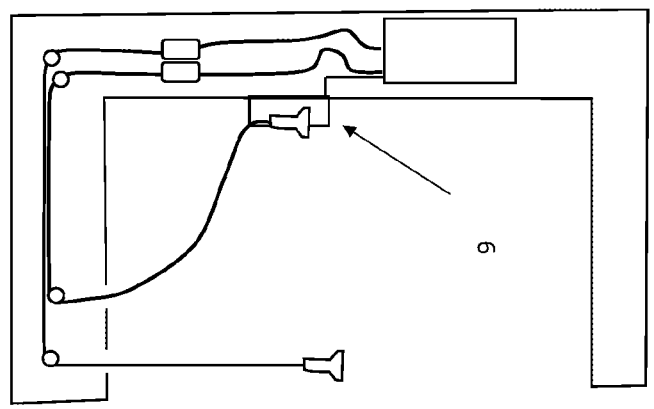

FIGS. 2a and 2b show a second exemplary embodiment of the system in two different configurations according to embodiments of the present disclosure. Both configurations substantially correspond to the embodiment of FIG. 1, except if differently described or shown.

In the exemplary configuration of FIG. 2a the medical device 3 is equipped with a magnetizable element, for example a metallic pad. The device 3 is thus attachable to a holding device in the form of an electro-magnet 9 (for example an electromagnetic pad). At the same time, the magnetizable element, comprising for example stainless steel, does not interfere with the signal acquisition and transmission though the probe and hence does not create noise during the imaging. Said electro-magnet is controllable by the processing and/or power unit. For example, in case the electro-magnet is deactivated, an attached device 3 is automatically detached due to gravity. For this purpose, the electro-magnet is advantageously arranged in an upper region of the vertical extension part 1a of the structure 1 (for instance on a structure surface or inside the structure), for example such that the cable of the device 3 has some margin. Hence, when the device 3 is detached, it moves down and get closer to the center of space 70 below the opening of the structure 1. In this embodiment, the retracted position of the medical device 3 corresponds to the state where it is attached to the electro-magnet and the first extended position corresponds to its detached state. The retracted position may also be referred to as a stand-by or parking position. Between the retracted and the first extended position the cable may not be moved in or out of the structure.

In FIG. 2a the cable also can have some margin inside the structure 3, which allows the medical device to be further extended from its first extended position to a second extended position (for example by pulling it out manually or by a motor).

The processing and/or power unit 50 may be in the vertical extension part of the structure. In this case the cable may again be equipped with a weight in this vertical extension part, which can at urge the cable back into the inside of the structure.

The configuration of FIG. 2b is substantially similar to that one of FIG. 2a. However, the cable of the medical device may additionally be equipped with magnetizable elements 10 (for example metallic rings) and respective magnets 11 may be arranged at the structure 1 above the magnet 9, for example on the vertical extension part 1a of the structure and/or its upper horizontal extension part 1c. Accordingly, not only the medical device 3 but also the cable can be attached to the structure. Desirably, the magnets 11 have such a force that they release the cable due to the gravity force applied to the medical device when released from electromagnet 9. Magnets 11 may also at least partially comprise electromagnets, for example arranged on the vertical extension part 1a above electromagnet 9.

The unit 50 may be arranged on the upper horizontal extension part of the structure 1. The section of the cable outside the structure may always have a length which allows to access the whole access space 70. However, in the retracted position of the device 3, the cable may be attached to the structure through magnets 11, such that it does not disturb the user or a patient from accessing the access space.

Generally, the magnets 9 and 11 may be electromagnets or may also be conventional magnets. In the latter case the user may manually detach the medical device, or the detachment may be triggered by another actuator, for example by a motorized wheel which can roll out the cable.

Figure 3:
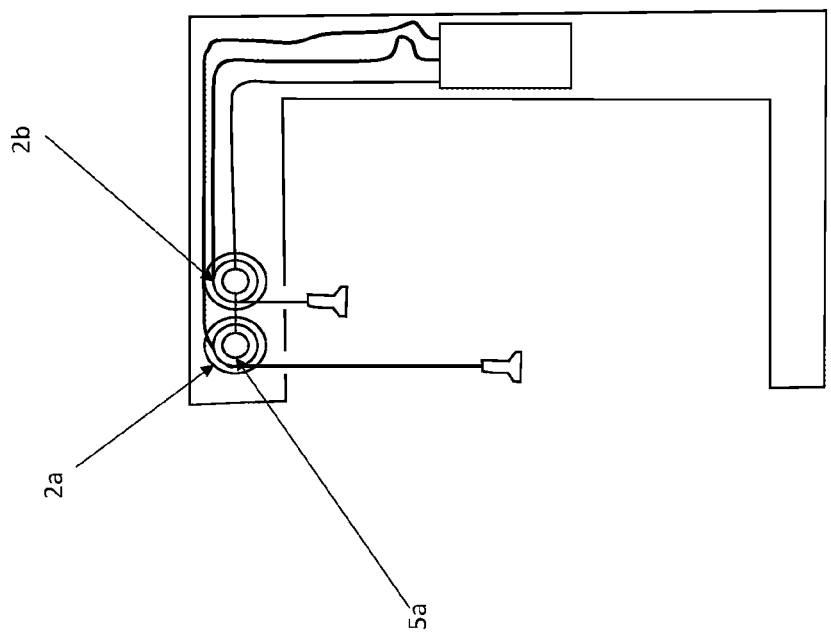
FIG. 3 shows a third exemplary embodiment of the system according to embodiments of the present disclosure.

FIG. 3 shows a third exemplary embodiment of the system according to embodiments of the present disclosure. In this configuration, the holding device may comprise a wheel in the form of a rewinding drum (or roll) 2b. Additionally, it comprises a rewinding spiral spring 2a. Said spring 2a may be configured to urge the roll 2b to rotate in a direction which retracts the cable 4. Accordingly, said spring 2a may replace the weight 8 of the cable in FIG. 1. The holding device may further comprise an actuator in the form of a motorized roller 5a with a clutch arranged inside the roll 2b.

Figure 4:
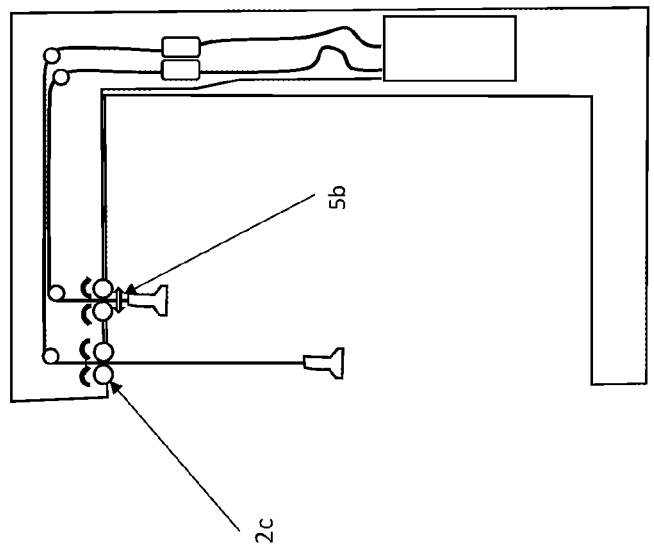
FIG. 4 shows a fourth exemplary embodiment of the system according to embodiments of the present disclosure.

FIG. 4 shows a fourth exemplary embodiment of the system according to embodiments of the present disclosure. In this configuration the holding device may be a clamping device arranged in or adjacent to the opening of the structure where the cable exits the structure. The clamping device may be configured to clamp and move the cable 4. Said clamping device may be realized for example by two transversally moveable and rotatable rollers 2c. For example, these rollers may be rotatable and/or transversally moveable by an actuator in the form of one or several electric motors. They may also be transversally moveable by an electromagnet constituting a further exemplary actuator. The actuator may be controlled by the processing and/or power unit 50. Moreover, the cables may be equipped with weights 8, as described above. In an alternative, clamping device may comprise instead of the rollers 2c a shape memory alloy may element configured to change its form such that the cable 4 can be clamped and released.

Accordingly, when the rollers rotate and at the same time clamp the cable, they may move the cable out of the structure 1, such that the medical device is moved from its retracted position to an extended position. In order to retract the device 3, the rollers 2c may be transversally moved (i.e. separated from each other as indicated by arrow 5b) to release the cable. As a consequence, the cable may automatically be retracted due the weight 8.

FIGS. 5a and 5b show a fifth exemplary embodiment of the system in two different configurations according to embodiments of the present disclosure. In these configurations the holding device does not hold the cable of the medical device. Instead, the medical device is attached to a tie (or electric cable) 4a which holds the device in any of its moveable positions.

The holding device is thus in the form of a rotatable tie holder which may have corresponding elements like one of the cable holders described above.

The cable 4 of the medical device may in this embodiment be outside the structure. They may be guided and/or hold by one or several cable guiding elements 12 attached to the structure 1. The cables may though also be arranged inside the structure, as shown in any of the other embodiments.

Generally, in any embodiment and as exemplarily shown in FIGS. 5a and 5b, the processing and/or power unit 50 may be arranged in an upper region of the structure 1, for example in an upper region of its vertical extension part 1a or on its upper horizontal extension part 1b. This has the advantage that, even if the cable length is limited to a maximum length (for example 2m), the proximity of the unit 50 to the access space 70 permits that the whole access space 70 can be reached by the medical device 3. the processing and/or power unit 50 may also be arranged to at least partly protrude from or be outside the structure 1. This has the advantage that the cable connectors (i.e. cable ports) of the unit 50 may be easily accessed by a user, for example in case a medical device has to be replaced or added.

FIGS. 6a to 6d show a sixth exemplary embodiment of the system according to embodiments of the present disclosure. In this embodiment the holding device 2 is in the form of a medical device cable holder configured to move out a cable of the medical device. More in particular, the cable holder comprises at least one wheel/pulley to arrange the cable in a folded manner. For example, the connector 51 of the cable at the processing and/or power unit 50 is on one side, together with the opening 30 of the structure 1 where the cable exits the structure 1. On the other side, the at least one wheel/pulley is arranged. The wheel/pulley is rotatable and transversely moveable, such that the distance between the wheel/pulley and the other side is changeable.

Figure 6C:
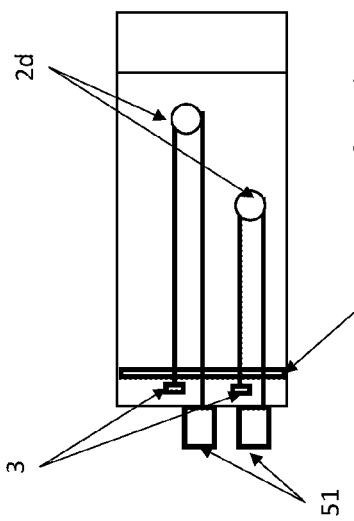
FIGS. 6a to 6d show a sixth exemplary embodiment of the system according to embodiments of the present disclosure.

The mounting structure 1 thus comprises a first accommodation space configured to accommodate the medical device cable holder and the cable of the medical device, such that the cable can be moved out by the medical device cable holder, and/or hide the cable within the mounting structure in the retracted position of the medical device. In the example of FIG. 6a-c the first accommodation space is arranged in the upper horizontal extension part of the structure 1. As it has been shown in other embodiments, it may also be arranged in other regions of the structure 1, for example in the vertical extension part.

FIG. 6a shows a schematic perspective side of an upper part of the system. In this example, the upper horizontal extension part of the structure 1 is open on its bottom side. In this area the cable holder 2 is arranged. The opening 30 (where the cable exits the structure 1) in this configuration is not on a bottom side but on a front side of the upper horizontal extension part 1c. Accordingly, the medical device 3 extends from this front side downwards and is hold by its cable.

FIG. 6b shows a side view of substantially the same configuration of the system 100. However, the opening 30 is arranged on the bottom side of the upper horizontal extension part of the structure 1, for example by a structural element which may also serve as a cable loop 30a (also cf. FIG. 6c). It is further shown that the unit 50 may be arranged in the upper horizontal extension part of the structure 1, for example such that the connector 51 is on the front side of the upper horizontal extension part. Accordingly, the connector 51 can easily be accessed by a user, as it may be outside the structure 1.

FIG. 6c shows a bottom view of the configuration of the system 100 of FIG. 6c. As shown, the wheel/pulley may be moved transversally along the upper horizontal extension part of the structure 1, in order to extend and retract the medical device 3. The wheel/pulley may be a tension idler 2d.

Figure 6D:
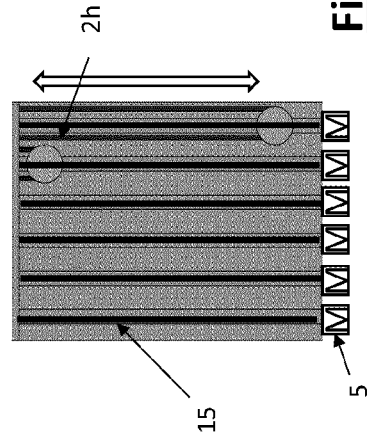
Figure 6B:
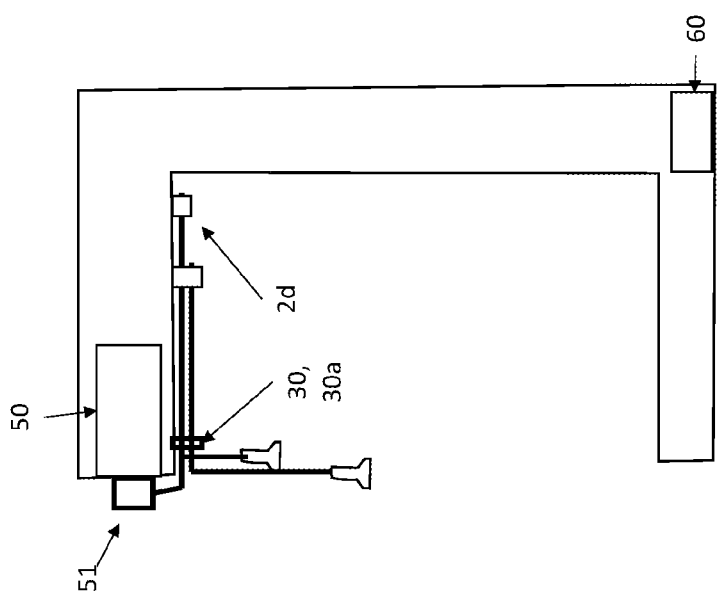
Figure 6A:
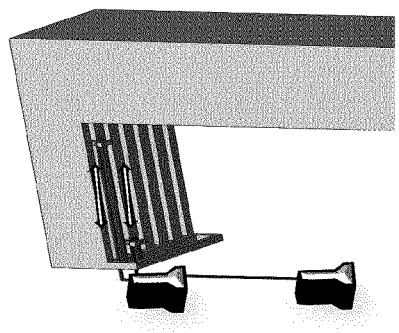

FIG. 6d shows the cable holder without the structure 1. Said cable holder may be arranged at different positions of the structure 1, for example on the surface of the structure body or inside the structure body. It may be arranged in or at the horizontal and/or the vertical extension part of the structure. As it is shown in FIG. 6d, the wheel may be guided in a transversal moving direction by a ball screw shaft or roller movement belt 15. Moreover, there may be provided a motor 5 to transversally move the wheel. In said example, the wheel may be freely rotatable. Examples of the motor 5 comprise an electric motor for moving the roller movement belt 15. In an alternative example the motor 5 may comprise a linear motor. The linear motor may for example move a maglev train comprising the wheel. In this example, the stator may constitute a track and a rotor may be included in the train. In a further alternative, instead of using a motor 5, a hydraulic actuator may be used, for example in the form of an extendable cylinder.

Generally, the structure may accommodate a power unit 60 separated to the processing unit 50 (cf. FIG. 6b). Said power unit may be arranged for example in the base of the structure 1 or in a lower part of the vertical extension part. Said power unit 60 may be configured to supply the unit 50 and/or the medical device 3 with power. For example, in such a case the unit 50 may also be merely a processing unit which controls the medical device and/or processes the data received from the medical device 3.

Figure 7A:
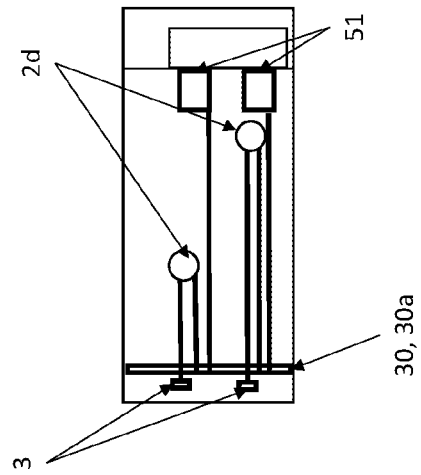
FIGS. 7a and 7b show a seventh exemplary embodiment of the system according to embodiments of the present disclosure.
Figure 7B:
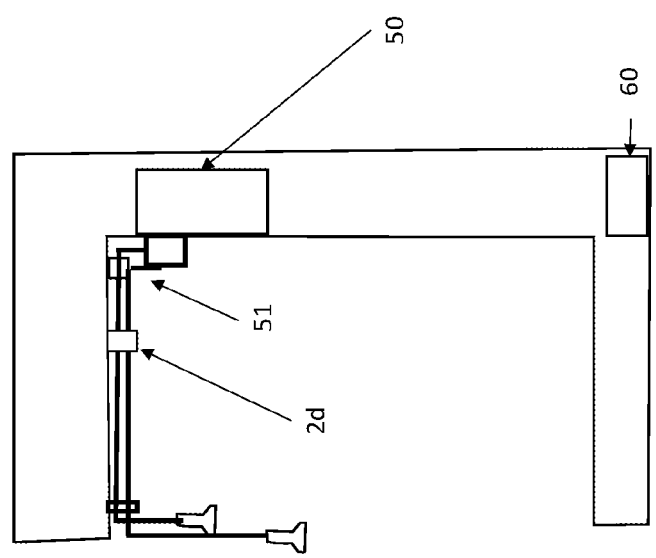
Figure 8D:
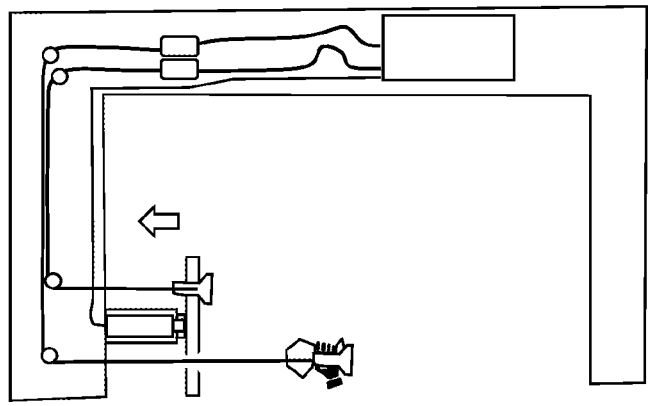
FIGS. 8a to 8d show an eighth exemplary embodiment of the system according to embodiments of the present disclosure.
Figure 8C:
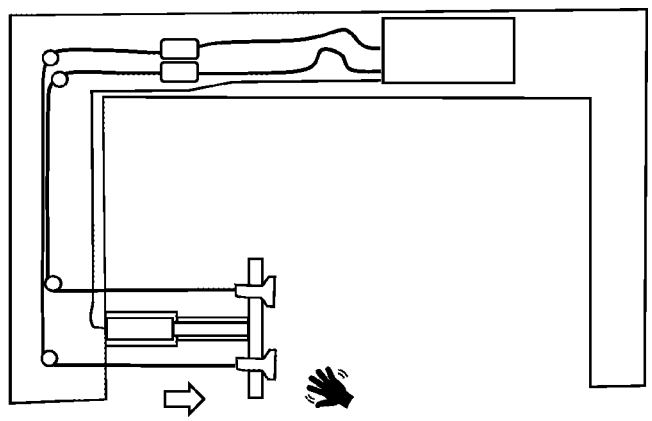
Figure 8B:
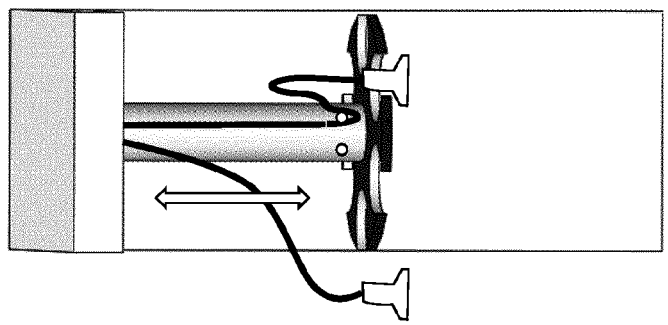
Figure 8A:
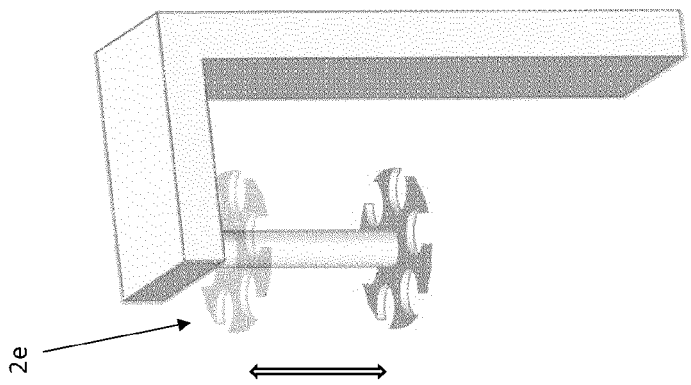

FIGS. 7a and 7b show a seventh exemplary embodiment of the system according to embodiments of the present disclosure. This embodiment substantially corresponds to the sixth embodiment. However, processing and/or power unit 50 is arranged in the vertical extension part of the structure. Alternatively, it may be arranged in the horizontal extension part on the side connected to the vertical extension part.

The cable may be arranged in a zig-zag form, or, in other words, in a multiply folded manner. The cable holder comprises for example a plurality of wheels/pulleys to arrange the cable. At least one wheel/pulley may be rotatable and/or transversely moveable, such that the distance between the wheels/pulleys is changeable. It is also possible to replace one of the wheels/pulleys, especially that one arranged at or close to the front side of the horizontal extension part by another element, for example a cable loop. Said further element (or the respective wheel) may be not transversally moveable, and optionally only rotatable.

Generally, when the cable is folded by the cable holder, the used wheel and/or pulley desirably has a minimum diameter which is defined as a function of a predetermined bendability parameter of the cable. This case in particular applies to ultrasound cables of conventional ultrasound probes, as described above. For example, the wheels/pulleys may have a diameter of least 6 cm, to respect the maximum bendability of the cable.

FIGS. 8a to 8d show an eighth exemplary embodiment of the system according to embodiments of the present disclosure. In this embodiment, the holding device may comprise a robotic arm configured to hold the medical device at moveable position. The robotic arm is extendable for this purpose. The robotic arm is arranged in a principally vertical direction from the bottom side of the horizontal extension part of the structure downwards to the access space. For example, the robotic arm may be an extendable cylinder (cf. especially FIGS. 8c and 8d). The robotic arm may be moved by an actuator, for example a hydraulic actuator. On its bottom side it may comprise one or several holders for medical devices. Accordingly, when the robotic arm is extended, the medical device arranged in a holder is extended, as well to its first extended position. The user may then grab the medical device (cf. FIG. 8c) and extend it further to its second extended position. For this purpose, the cable or tie of the medical device may be further extendable out of the structure 1, as described above.

FIGS. 9a and 9b show a ninth exemplary embodiment of the system according to embodiments of the present disclosure. Said embodiment may correspond to any of the other embodiments. In addition, it comprises an illumination element 14 (for example a lamp) configured to illuminate the access space. In one configuration shown in FIG. 9a the illumination element 14 may be hold by a holding device in an extendable manner, similar to the medical device 3. In other words, the holding device of the illumination element 14 may correspond to any of the described holding devices 2 which hold a medical device 3. The illumination element 14 may thus be extended from the structure 1 when needed. This may be triggered by for example a user command, a medical workflow algorithm or any AI algorithm. In a further example, the system may comprise a light sensor, wherein the output signal of the sensor is used to trigger the extension and activation of the illumination element 14.

In one configuration shown in FIG. 9b the illumination element 14 may be hold by the structure 1, for example by its vertical extension part. Generally, instead of the illumination device or in addition thereto, the system may comprise a camera configured to take images and/or a video of the medical examination and/or treatment.

FIGS. 10a and 10b show an tenth exemplary embodiment of the system according to embodiments of the present disclosure. Said embodiment may correspond to any of the other embodiments. In addition, it comprises a gel ejector holding device retained by the mounting structure and configured to hold a gel ejector 13 at a changeable position above the access space via its gel tube. Accordingly, the gel injector may be attached, be extendable and provided by the system in a similar way like the one or several medical devices. The gel is intended to be applied on the surface of a patient during examination with an ultrasound probe 3.

The mounting structure may comprise a fourth accommodation space configured for accommodating a gel reservoir 80 connected via a gel tube to the gel ejector (for example a gel pistol). The gel reservoir may be arranged adjacent to the processing and/or power unit 50, such that the unit 50 can be cooled by the gel in the reservoir and at the same time the gel can be heated. It is also possible that the system is equipped with an additional heating device to heat the gel provided to patient, for example to have a temperature close to a human body temperature. In one example, the heating device may be an electrical resistance. The heating device may be configured to heat the gel in the gel reservoir and/or in the gel tube. Furthermore, a gel pump may be used to transport the gel from the reservoir to the gel ejector.

The holding device 2 of the gel ejector may correspond to any of the described holding devices 2 which hold a medical device 3. In particular it may comprise rewinding spiral spring 2a. Said spring 2a may be configured to rotate the roll 2b in a direction which retracts the cable 4. Additionally, or alternatively, the cable may be equipped with a weight. The holding device 2 may further comprise an actuator in the form of a motorized roller 5a with a clutch arranged inside the roll 2b. The holding device may also comprise a wheel in the form of a rewinding roll.

In the configuration shown in FIG. 10a the gel ejector exits the structure 1 via an opening on the bottom side of the upper horizontal extension part, for example similar like the medical device. In the configuration shown in FIG. 10b, which is principally similar to that one of FIG. 10a, the gel ejector exits the structure 1 via an opening in the vertical extension part of the structure 1.

Generally, and as shown in FIGS. 10a and 10b, the base of the structure 1 may also have wheels, such that the system can easily be moved, for example from one room to another. Additionally, the system may comprise, separate to the structure 1, a table or any other external base or stretcher for placing a patient.

FIGS. 11a to 11d show a eleventh exemplary embodiment of the system according to embodiments of the present disclosure. Said embodiment may correspond to any of the other embodiments. In addition, it may comprise a third accommodation space of the structure comprising a maintenance device.

Figure 11B:
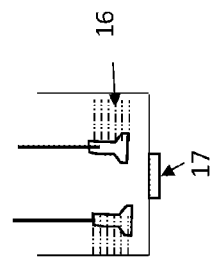
FIGS. 11a to 11d show a eleventh exemplary embodiment of the system according to embodiments of the present disclosure.
Figure 11D:
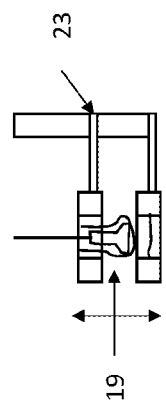
Figure 11C:
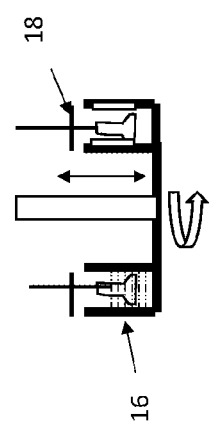
Figure 11A:
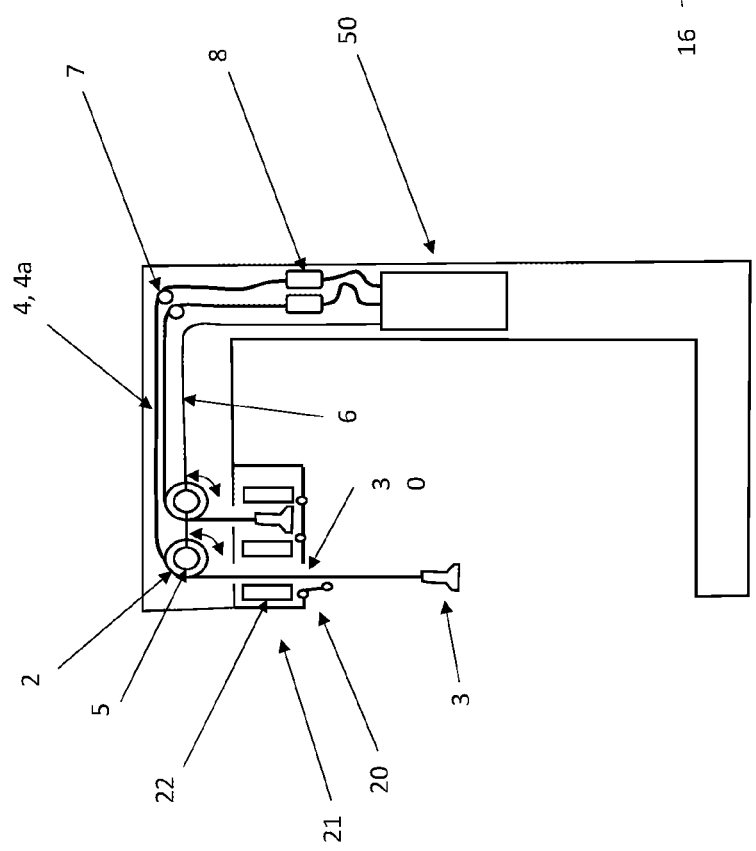

In the configuration of FIG. 11a the third accommodation space is a cleaning box 20. Said box may have an opening optionally with a closeable door configured to permit the medical device 3 to be moved out of the box. The medical device is inside the box in its retracted position. The box further has a cleaning system 21, for example in the form of one or several brushes 22. The cleaning system may be controlled by the processing unit 50, for example to automatically clean a medical device after its retraction. The cleaning may also be triggered manually by a user command. It is further possible that cleaning is carried out only when necessary, based as example on a predefined number of sequences or, for example, the box 20 may comprise one or several sensors (for example optical sensors) to measure whether cleaning is required. The box may be configured to accommodate and clean several medical devices 3.

In FIG. 11*b* a different configuration of the cleaning box is shown. Here, instead of or additionally to the brushes, one or several nozzles may be provided to clean the medical device 3 with a gas and/or a liquid (for example water and or disinfectant). The box may hence also comprise a drain or drain pump 17 to eject the liquid from the box.

Beside the above-mentioned cleaning options, the box may be configured for at least one of the following functions: disinfecting the medical device, for example using ultraviolet waves and/or a disinfecting liquid, testing and status control using at least one scanner to scan the medical device, and protecting the medical device from exterior influences.

In FIG. 11*b* a further possible configuration of the cleaning box is shown. The box may have the form of a rotatable carousel with at least one maintenance space 16 which has at least one of the above-mentioned maintenance functions. The medical device and/or its cable may further be equipped with a horizontally extending overhead probe cover 18. Said cover may for example also be configured to close the maintenance space 16 when the medical device 3 is placed in its inside. In case a plurality of medical devices are used, the system may comprise a respective plurality of covers 18 which are individually openable. In an alternative, it may comprise one central cover for all medical devices.

The carousel may be rotatable. Accordingly, a medical device placed in a maintenance space 16 cable retracted, to allow the carousel to rotate. The carousel may thus rotate to a position where it has an opening below the retracted medical device. Said opening permits the medical device to be moved downwardly to its first extended position.

In the configuration of FIG. 11*d* the maintenance space 16 or another circumferential section of the carousel comprises a covering device 19 configured to provide protection sheaths. Said sheaths may for example have a bag form adapted to the size of the medical device 3. Accordingly, the medical device may be moved in and/or through said covering device 19, such that the device 3 is automatically covered by a protection sheath. This step may be done at each use of a protection device, such that the medical device is covered for each procedure, in order to prevent cross-contamination and reduce the risk of healthcare-associated infections. The covering device 19 may also be configured to remove a used protection sheath from the medical device. It is also possible that the carousel comprises another circumferential section with a respectively configured sheath removal device. Alternatively, the protection cove may be manually removeable by a user.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Although the present disclosure herein has been described with reference to particular embodiments, it is to be understood that these embodiments are merely illustrative of the principles and applications of the present disclosure.

It is intended that the specification and examples be considered as exemplary only, with a true scope of the disclosure being indicated by the following claims.

The invention claimed is:

1. A system for providing a medical device, the system comprising:
a mounting structure arranged adjacent to and/or at least partially above an access space where an object to be accessed by the medical device can be placed, and
a holding device retained by the mounting structure and configured to hold the medical device at a changeable position above the access space, the holding device being arranged within the mounting structure,
wherein the holding device is configured such that the medical device is moved from a retracted position to a first extended position upon a first predefined event;
wherein the holding device is configured to move the medical device from the first extended position to a second extended position upon a second predefined event, the second extended position being closer to the access space and/or below the first extended position; and
wherein the second predefined event comprises at least one of:
a sensor signal from a sensor of the medical device indicating that a user has touched the medical device, and
a sensor signal from a sensor indicating that a user has pulled the medical device toward the second extended position.

2. The system according to claim 1, wherein the first extended position is at least one of closer to the access space, and below the retracted position.

3. The system according to claim 1, wherein at least one of:
the medical device comprises at least one of:
an electric or electronic medical device,
an examination probe,
a medical sensor,
a laser device, and
an ultrasound examination probe, and
the holding device comprises at least one of:
a medical device cable holder configured to move out a cable of the medical device upon the first predefined event, such that the medical device is moved from the retracted to the extended position,
a tie holder and a tie configured to hold the medical device in the retracted position, wherein upon the predefined first event the tie is moved out by the tie holder, such that the medical device moves to the extended position,
an electromagnet configured to hold the medical device in the retracted position, wherein upon the first predefined event the electromagnet is turned off, such that the medical device moves to the extended position, and
a robotic arm configured to hold the medical device at the retracted position, wherein upon the first predefined event the robotic arm moves the medical device to the extended position.

4. The system according to claim 3, wherein the mounting structure comprises a first accommodation space configured to at least one of:
accommodate the medical device cable holder and the cable of the medical device, such that the cable can be moved out by the medical device cable holder, and hide the cable within the mounting structure in the retracted position of the medical device.

5. The system according to claim 4, wherein the medical device is connected via a data cable to a processing unit which processes medical data received from the medical device via the data cable, and the mounting structure comprises a second accommodation space configured to accommodate the processing unit above the access space.

6. The system according to claim 5, wherein the mounting structure comprises a third accommodation space configured to accommodate the medical device in its retracted position and/or above the access space.

7. The system according to claim 6, wherein the third accommodation space comprises a maintenance device configured for at least one of:
   disinfecting and/or cleaning the medical device,
   testing and status control using at least one scanner to scan the medical device, and
   protecting the medical device from exterior influences.

8. The system according to claim 6, wherein a distance from the second accommodation space via the first accommodation space and the third accommodation space to the access space is less than a distance threshold which is defined as a function of a length of the medical device cable.

9. The system according to claim 3, wherein the medical device cable holder comprises at least one of a wheel and a pulley, which moveably supports the medical device cable.

10. The system according to claim 9, wherein the at least one of the wheel and the pulley has a minimum diameter which is defined as a function of a predetermined bendability parameter of the cable, the bendability parameter comprising among others at least one of: a cable thickness, a cable type, and a cable material.

11. The system according to claim 1, further comprising an actuator configured to actuate the holding device, such that the medical device is moved from the retracted position to the first extended position upon the first predefined event.

12. The system according to claim 11, wherein the actuator comprises at least one of:
   a hydraulic actuator,
   an electronically and/or electrically controlled actuator,
   an electric motor,
   a linear motor, and
   an electro-magnetic actuator.

13. The system according to claim 1, wherein the medical device is connected via a power cable to a power unit which powers the medical device via the power cable, the power unit being accommodated in the mounting structure.

14. The system according to claim 13, wherein the medical device wirelessly transmits medical data to a processing unit which is separate to the power unit and/or remote to the system.

15. The system according to claim 1,
   wherein the system is configured for providing a plurality of medical devices and comprises a respective plurality of holding devices,
   each holding device is retained by the mounting structure and configured to hold a medical device among the plurality of medical devices at a changeable position above the access space,
   wherein the system is configured to actuate a first holding device among the plurality of holding devices to move a respective first medical device from the retracted position to the first extended position upon the first predefined event.

16. The system according to claim 1, wherein the holding device is configured to move the medical device from the first extended position or a second extended position to the retracted position upon a third predefined event.

17. The system according to claim 16, wherein the third predefined event comprises at least one of:
   the end of a predefined and/or customisable medical workflow,
   a user command stopping a current medical workflow or indicating that a current workflow is to be continued with another medical device, and
   a command triggered by an algorithm indicating that a current workflow is to be continued with another medical device.

18. The system according to claim 16, wherein, in case the third predefined event comprises a command that a current workflow is to be continued with another medical device, the first medical device is retracted from the second extended position to the retracted position, and a second selected medical device is extended from the retracted position to the first extended position upon the third predefined event.

19. The system according to claim 1, wherein the mounting structure comprises:
   a fourth accommodation space configured for accommodating a gel reservoir connected via a gel tube to a gel ejector, and
   a gel ejector holding device retained by the mounting structure and configured to hold the gel ejector at a changeable position above the access space,
   wherein the gel ejector holding device is configured to move the gel ejector at least one of:
      from a retracted position to the first extended position upon a fourth predefined event,
      from the first extended position to a second extended position upon a second predefined event, the second extended position being closer to the access space, and/or below the first extended position, and
      from the first or second extended position to the retracted position upon a fifth predefined event.

20. The system according to claim 1, wherein the first predefined event comprises at least one of:
   a user command,
   a sensor signal,
   a command triggered by an algorithm comprising:
      a predefined and/or customisable medical workflow algorithm, and
      an artificial intelligence algorithm.

21. A medical platform comprising:
   the medical device, and
   the system according to claim 1.

22. The medical platform according to claim 21, further comprising:
   a processing unit configured to process medical data received from the medical device,
   the processing unit being configured to carry out a medical workflow algorithm and/or an artificial intelligence algorithm, and to transmit a command to the system triggered by any of the algorithms, wherein the command constitutes at least one of the first predefined event, a second predefined event, a third predefined event, and a fourth predefined event.

23. A method for providing a medical device, the method comprising:
   arranging a mounting structure adjacent to and/or at least partially above an access space where an object to be accessed by the medical device can be placed,
   providing a holding device retained by the mounting structure, the holding device being arranged within the mounting structure, wherein:

the holding device holds the medical device at a changeable position above the access space, the holding device actuates upon a first predefined event such that the medical device moves from a retracted position to a first extended position;

the holding device is configured to move the medical device from the first extended position to a second extended position upon a second predefined event, the second extended position being closer to the access space, and/or below the first extended position; and the second predefined event comprises at least one of:

a sensor signal from a sensor of the medical device indicating that a user has touched the medical device, and a sensor signal from a sensor indicating that a user has pulled the medical device toward the second extended position.

* * * * *